(12) United States Patent
Sim et al.

(10) Patent No.: US 10,040,803 B2
(45) Date of Patent: Aug. 7, 2018

(54) 4-((2-ACRYLAMIDOPHENYL)AMINO)THIENO[3,2-D]PYRIMIDINE-7-CARBOXAMIDE DERIVATIVES AS PROTEIN KINASE INHIBITORS

(71) Applicant: KOREA INSTITUTE OF SCIENCE AND TECHNOLOGY, Seoul (KR)

(72) Inventors: Tae Bo Sim, Seoul (KR); Ho Jong Yoon, Seoul (KR); In Jae Shin, Seoul (KR); Yun Ju Nam, Seoul (KR); Hwan Geun Choi, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/821,962

(22) Filed: Nov. 24, 2017

(65) Prior Publication Data
US 2018/0148459 A1 May 31, 2018

(30) Foreign Application Priority Data

Nov. 25, 2016 (KR) .................. 10-2016-0158186

(51) Int. Cl.
*C07D 495/02* (2006.01)
*C07D 495/04* (2006.01)
*A61P 35/00* (2006.01)

(52) U.S. Cl.
CPC ............ *C07D 495/04* (2013.01); *A61P 35/00* (2018.01)

(58) Field of Classification Search
CPC ........................ C07D 495/02; C07D 495/04
See application file for complete search history.

(56) References Cited

U.S. PATENT DOCUMENTS

| 9,340,514 B2 | 5/2016 | Bifulco, Jr. et al. |
| 9,434,697 B2 | 9/2016 | Reynolds et al. |
| 2007/0099877 A1 | 5/2007 | Cai et al. |

FOREIGN PATENT DOCUMENTS

| KR | 10-2009-0047391 A | 5/2009 |
| KR | 10-2011-0073482 A | 6/2011 |
| KR | 10-1147550 B1 | 5/2012 |
| KR | 10-1559114 B1 | 1/2016 |

OTHER PUBLICATIONS

Hagel et al., "First Selective Small Molecule Inhibitor of FGFR4 for the Treatment of Hepatocellular Carcinomas with an Activated FGFR4 Signaling Pathway", Cancer Discovery, vol. 5, 2015, pp. 424-437.
Turkington et al., "Fibroblast growth factor receptor 4 (FGFR4): a targetable regulator of drug resistance in colorectal cancer", Cell Death and Disease, vol. 5, e1046, 2014, 11 pages.

*Primary Examiner* — Bruck Kifle
(74) *Attorney, Agent, or Firm* — Birch, Stewart, Kolasch & Birch, LLP

(57) ABSTRACT

The present invention relates to a novel 4-((2-acrylamidophenyl)amino)thieno[3,2-d]pyrimidine-7-carboxamide compound, an anticancer agent containing the compound as an active ingredient and an intermediate compound for preparing the compound.

8 Claims, No Drawings

4-((2-ACRYLAMIDOPHENYL)AMINO) THIENO[3,2-D]PYRIMIDINE-7-CARBOXAMIDE DERIVATIVES AS PROTEIN KINASE INHIBITORS

CROSS-REFERENCE TO RELATED APPLICATIONS

This application claims, under 35 U.S.C. § 119, the priority of Korean Patent Application No. 10-2016-0158186, filed on Nov. 25, 2016, in the Korean Intellectual Property Office, the disclosure of which is incorporated herein by reference in its entirety.

BACKGROUND

(a) Technical Field

The present invention relates to a novel 4-((2-acrylamidophenyl)amino)thieno[3,2-d]pyrimidine-7-carboxamide compound, an anticancer agent containing the compound as an active ingredient and an intermediate compound for preparing the compound.

(b) Background Art

A protein kinase is an enzyme which catalyzes phosphorylation of hydroxyl groups on the tyrosine, serine and threonine residues of a protein. It plays an important role in growth factor signal transduction which induces the growth, differentiation and proliferation of cells.

To maintain homeostasis, it is necessary to keep a good balance in the turning on and off of the signal transduction system. However, mutation or overexpression of specific protein kinases disrupts the signal transduction system in normal cells and causes various diseases including cancers, inflammations, metabolic diseases, brain diseases, etc. Recently, researches are being conducted to develop an anticancer agent using a compound having selective inhibition activity against specific kinases among various protein kinases.

FGFs are fibroblast growth factors transducing signals. They regulate fundamental signaling pathways via fibroblast growth factor receptors (FGFRs) and are expressed in wide variety of tissues. The fibroblast growth factor receptors (FGFRs) include FGFR1, FGFR2, FGFR3 and FGFR4 and the FGFR-FGF signal transduction system stimulates cellular proliferation, migration and differentiation and plays a major role in bone and limb development, wound healing, tissue repair, hematosis, angiogenesis and oncogenesis.

It is reported that the overexpression, mutation, translocation and truncation of FGFRs are associated with a number of human cancers, including myeloma, breast cancer, stomach cancer, colon cancer, bladder cancer, pancreatic cancer and hepatocellular carcinoma. Hepatocellular carcinoma (HCC) is one of the leading global causes for cancer-related deaths, resulting in over half a million fatalities per year. It is known that FGFR4 may play an important role in the development and/or progress of hepatocellular carcinoma (HCC).

Although many FGFR inhibitors inhibiting FGFR1, FGFR2 and FGFR3 are under clinical tests at present, a selective FGFR4 inhibitor that can be administered to patients has not been reported. Therefore, development of a novel drug that can selectively inhibit FGFRs is necessary.

REFERENCES OF THE RELATED ART

Non-Patent Documents (Non-patent document 1) "First Selective Small Molecule Inhibitor of FGFR4 for the Treatment of Hepatocellular Carcinomas with an Activated FGFR4 Signaling Pathway", *Cancer Discovery* 22015 April; 5(4): 424-37.

(Non-patent document 2) "Fibroblast growth factor receptor 4 (FGFR4): a targetable regulator of drug resistance in colorectal cancer", *Cell Death and Disease* (2014) 5, e1046.

SUMMARY

The present invention is directed to providing a 4-((2-acrylamidophenyl)amino)thieno[3,2-d]pyrimidine-7-carboxamide compound having inhibition activity against a protein kinase.

The present invention is also directed to providing an anticancer agent containing the 4-((2-acrylamidophenyl)amino)thieno[3,2-d]pyrimidine-7-carboxamide compound as an active ingredient.

The present invention is also directed to providing a novel intermediate compound for synthesizing the 4-((2-acrylamidophenyl)amino)thieno[3,2-d]pyrimidine-7-carboxamide compound.

In an aspect, the present invention provides a compound selected from a group consisting of a 4-((2-acrylamido-6-methylphenyl)amino)thieno[3,2-d]pyrimidine-7-carboxamide compound represented by Chemical Formula 1, a pharmaceutically acceptable salt thereof, a hydrate thereof, a solvate thereof and an isomer thereof:

[Chemical Formula 1]

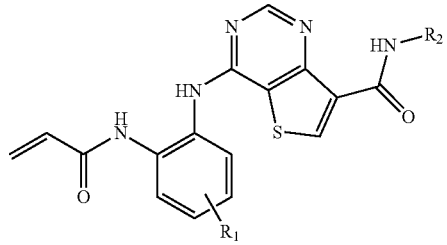

wherein $R_1$ is a hydrogen atom or a $C_1$-$C_6$ alkyl group, $R_2$ is a $C_1$-$C_6$ alkyl group, a $C_1$-$C_6$ hydroxyalkyl group, a $C_6$-$C_{12}$ aryl group or a 5- or 6-membered heteroaryl group containing 1-3 nitrogen atom(s), and the aryl group or the heteroaryl group may be respectively substituted or unsubstituted with 1-2 substituent(s) selected from a group consisting of $C_1$-$C_6$ alkyl, a halogen, $C_1$-$C_6$ alkoxy,

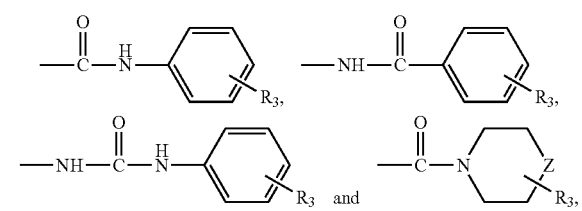

wherein Z is CHR$_3$, NR$_3$ or O and R$_3$ is a hydrogen atom, a C$_1$-C$_6$ alkyl group, a C$_1$-C$_6$ haloalkyl group or a C$_1$-C$_6$ alkoxy group.

The 4-((2-acrylamidophenyl)amino)thieno[3,2-d]pyrimidine-7-carboxamide compound represented by Chemical Formula 1 according to the present invention has a superior ability of inhibiting the activity of a protein kinase and also has a very highly selective inhibition activity. Specifically, the protein kinase may include ABL1, ABL2, ACK1, ARAF, BLK, BRAF, BRK, BTK, CSK, c-SRC, DDR1, DDR2, EGFR, FGFR1, FGFR2, FGFR3, FGFR4, FMS, FYN, GCK, HCK, JAK1, JAK2, JNK2, KDR, MAP4K5, LCK, LRRK2, LYN, p38α, PDGFRα, PDGFRβ, PYK2, RAF1, RET, ROS, SIK2, SRMS, TEC, TRKA, TRKB, TRKC, TXK, TYK2, YES, ZAK, etc. Accordingly, the compound according to the present invention may be used to treat, prevent or alleviate a cancer caused by abnormal cell growth. The cancer that may be treated, prevented or alleviated by the compound according to the present invention may include stomach cancer, lung cancer, liver cancer, colon cancer, small intestine cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, kidney cancer, sarcoma, prostate cancer, urethral cancer, bladder cancer, blood cancer (including leukemia, multiple myeloma and myelodysplastic syndrome), lymphoma (including Hodgkin's disease and non-Hodgkin lymphoma), psoriasis, fibroadenoma, etc.

In addition, because the 4-((2-acrylamidophenyl)amino)thieno[3,2-d]pyrimidine-7-carboxamide compound according to the present invention covalently binds to FGFR4 irreversibly, it has selectivity not only against other protein kinases but also against FGFR1, FGFR2 and FGFR3. Accordingly, due to the selective inhibition activity against FGFRs, the compound according to the present invention can be used to treat, prevent and alleviate myeloma, breast cancer, stomach cancer, colon cancer, bladder cancer, pancreatic cancer and hepatocellular carcinoma.

DETAILED DESCRIPTION

The present invention provides a compound selected from a group consisting of a 4-((2-acrylamido-6-methylphenyl)amino)thieno[3,2-d]pyrimidine-7-carboxamide compound represented by Chemical Formula 1, a pharmaceutically acceptable salt thereof, a hydrate thereof, a solvate thereof and an isomer thereof:

[Chemical Formula 1]

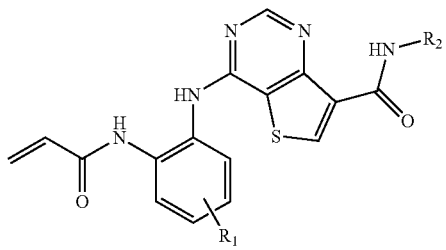

wherein
R$_1$ is a hydrogen atom or a C$_1$-C$_6$ alkyl group,
R$_2$ is a C$_1$-C$_6$ alkyl group, a C$_1$-C$_6$ hydroxyalkyl group, a C$_6$-C$_{12}$ aryl group or a 5- or 6-membered heteroaryl group containing 1-3 nitrogen atom(s), and the aryl group or the heteroaryl group may be respectively substituted or unsubstituted with 1-2 substituent(s) selected from a group consisting of C$_1$-C$_6$ alkyl, a halogen, C$_1$-C$_6$ alkoxy,

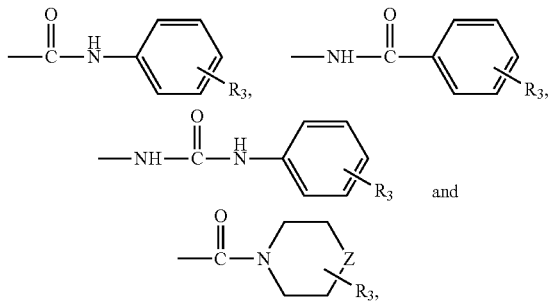

wherein Z is CHR$_3$, NR$_3$ or O and R$_3$ is a hydrogen atom, a C$_1$-C$_6$ alkyl group, a C$_1$-C$_6$ haloalkyl group or a C$_1$-C$_6$ alkoxy group.

The compound represented by Chemical Formula 1 according to the present invention may be a pharmaceutically acceptable salt. The pharmaceutically acceptable salt should have low toxicity in the human body and should not negatively affect the biological activity and physicochemical properties of the parent compound. The pharmaceutically acceptable salt may be a salt formed from a reaction between the base compound of Chemical Formula 1 and a pharmaceutically acceptable free acid. The pharmaceutically acceptable salt may be prepared by a method commonly employed in the related art. The free acid that may be used to prepare the pharmaceutically acceptable salt may be an inorganic acid or an organic acid. The inorganic acid may be hydrochloric acid, sulfuric acid, nitric acid, phosphoric acid, perchloric acid, bromic acid, etc. The organic acid may be acetic acid, methanesulfonic acid, ethanesulfonic acid, p-toluenesulfonic acid, trifluoroacetic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, etc.

The compound represented by Chemical Formula 1 according to the present invention also includes a hydrate or a solvate. The hydrate or the solvate may be prepared by a commonly employed method. For example, it may be prepared by dissolving the base compound of Chemical Formula 1 in a water-miscible solvent such as methanol, ethanol, acetone and 1,4-dioxane, adding a free acid or a free base and then performing crystallization or recrystallization.

The compound represented by Chemical Formula 1 according to the present invention may have one or more chiral center and such a compound may exist as an enantiomer or a diastereomer. Accordingly, the present invention includes the isomers or a mixture of the isomers. The isomer may be separated or resolved by a commonly employed method or may be obtained by a commonly employed stereospecific or asymmetric synthesis method.

The present invention also includes a radioactive derivative of the compound represented by Chemical Formula 1. The radioactive compound is useful in biological researches.

Hereinafter, the substituents used to define the compound according to the present invention are described in more detail.

In the present invention, the term 'halo' or 'halogen atom' can be used interchangeably and means chloro, fluoro, bromo or iodo.

In the present invention, 'alkyl' refers to a linear, branched or cyclic aliphatic saturated hydrocarbon group having 1-10 carbon atoms(s), specifically 1-6 carbon atoms(s), more specifically 1-4 carbon atoms(s). Specific examples of the alkyl group include a methyl group, an ethyl group, a n-propyl group, an isopropyl group, a cyclopropyl group, a cyclopropylmethyl group, a n-butyl group, an isobutyl group, a tert-butyl group, a cyclobutyl group, a n-pentyl group, an isopentyl group, a neopentyl group, a tert-pentyl group, a cyclopentyl group, a n-hexyl group, an isohexyl group, a cyclohexyl group, a n-heptyl group, a n-octyl group, etc.

In the present invention, a 'haloalkyl group' refers to a linear or starched carbon chain containing 1-13 halogen atom(s) such as fluorine, chlorine, bromine and iodine and having 1-10 carbon atom(s). Specific examples of the haloalkyl group may include a fluoromethyl group, a trifluoromethyl group, a 1,2-dichloroethyl group, a 1,1-dichloroethyl group, a pentafluoroethyl group, etc.

In the present invention, an 'alkoxy group' refers to —O—($C_1$-$C_{10}$ alkyl). Specific examples may include a methoxy group, an ethoxy group, a propoxy group, a tert-butoxy group, a cyclohexyloxy group, etc.

In the present invention, 'aryl' refers to a monocyclic, bicyclic or tricyclic aromatic hydrocarbon group having 6-12 carbon atoms. Specific examples of the aryl group may include a phenyl group, a naphthyl group, etc.

In the present invention, 'heteroaryl' refers to a 5- or 6-membered aromatic cyclic group containing 1-3 nitrogen (N) atom(s). Specific examples of the heteroaryl may include a pyrrolyl group, a pyrazolyl group, an imidazolyl group, a pyridinyl group, a pyrazinyl group, a pyridazinyl group, a pyrimidinyl group, etc.

Specifically, in the compound represented by Chemical Formula 1, $R_1$ may be a $C_1$-$C_6$ alkyl group and $R_2$ may be a $C_1$-$C_6$ alkyl group or a $C_1$-$C_6$ hydroxyalkyl group.

Specifically, in the compound represented by Chemical Formula 1, $R_1$ may be a $C_1$-$C_6$ alkyl group, $R_2$ may be a phenyl group or a naphthalenyl group, and the phenyl group may be substituted or unsubstituted with 1-2 substituent(s) selected from a group consisting of $C_1$-$C_6$ alkyl, $C_1$-$C_6$ alkoxy,

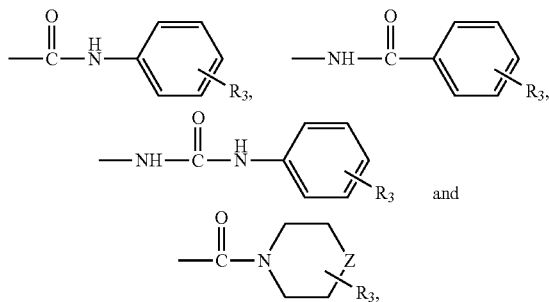

wherein Z is an oxygen (O) atom and $R_3$ is a $C_1$-$C_6$ alkyl group, a $C_1$-$C_6$ haloalkyl group or a $C_1$-$C_6$ alkoxy group.

Specifically, in the compound represented by Chemical Formula 1, $R^1$ may be a $C_1$-$C_6$ alkyl group, $R_2$ may be a pyrazolyl group or a pyridinyl group, and the pyrazolyl group or the pyridinyl group may be respectively substituted or unsubstituted with 1-2 substituent(s) selected from a group consisting of a $C_1$-$C_6$ alkyl group.

Specific examples of the compound represented by Chemical Formula 1 are as follows:
Compound 1. 4-((2-acrylamido-6-methylphenyl)amino)-N-(3,5-dimethoxyphenyl)thieno[3,2-d]pyrimidine-7-carboxamide;
Compound 2. 4-((2-acrylamido-6-methylphenyl)amino)-N-(2-methyl-5-(3-(trifluoromethyl)benzamido)phenyl)thieno[3,2-d]pyrimidine-7-carboxamide;
Compound 3. 4-((2-acrylamido-6-methylphenyl)amino)-N-(naphthalen-1-yl)thieno[3,2-d]pyrimidine-7-carboxamide;
Compound 4. 4-((2-acrylamido-6-methylphenyl)amino)-N-(2-methoxy-4-(morpholine-4-carbonyl)phenyl)thieno[3,2-d]pyrimidine-7-carboxamide;
Compound 5. 4-((2-acrylamido-6-methylphenyl)amino)-N-(1-methyl-1H-pyrazol-3-yl)thieno[3,2-d]pyrimidine-7-carboxamide;
Compound 6. 4-((2-acrylamido-6-methylphenyl)amino)-N-(5-(3-(2-methoxyphenyl)ureido)-2-meth ylphenyl)thieno[3,2-d]pyrimidine-7-carboxamide;
Compound 7. 4-((2-acrylamido-6-methylphenyl)amino)-N-(2-hydroxyethyl)thieno[3,2-d]pyrimidine-7-carboxamide;
Compound 8. 4-((2-acrylamido-6-methylphenyl)amino)-N-cyclopropylthieno[3,2-d]pyrimidine-7-carboxamide; or
Compound 9. 4-((2-acrylamido-6-methylphenyl)amino)-N-(6-methylpyridin-3-yl)thieno[3,2-d]pyrimidine-7-carboxamide.

The present invention also provides a pharmaceutical composition containing the compound represented by Chemical Formula 1, a pharmaceutically acceptable salt thereof, a solvate thereof or a hydrate thereof as an active ingredient.

The pharmaceutical composition according to the present invention has a superior ability of inhibiting the activity of a protein kinase. Specifically, the protein kinase may include ABL1, ABL2, ACK1, ARAF, BLK, BRAF, BRK, BTK, CSK, c-SRC, DDR1, DDR2, EGFR, FGFR1, FGFR2, FGFR3, FGFR4, FMS, FYN, GCK, HCK, JAK1, JAK2, JNK2, KDR, MAP4K5, LCK, LRRK2, LYN, p38α, PDGFRα, PDGFRβ, PYK2, RAF1, RET, ROS, SIK2, SRMS, TEC, TRKA, TRKB, TRKC, TXK, TYK2, YES, ZAK, etc.

Accordingly, the pharmaceutical composition of the present invention may be used to treat, prevent or alleviate a cancer caused by abnormal cell growth. The cancer that may be treated, prevented or alleviated by the compound of the present invention may include stomach cancer, lung cancer, liver cancer, colon cancer, small intestine cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, kidney cancer, sarcoma, prostate cancer, urethral cancer, bladder cancer, blood cancer (including leukemia, multiple myeloma and myelodysplastic syndrome), lymphoma (including Hodgkin's disease and non-Hodgkin lymphoma), psoriasis, fibroadenoma, etc.

In particular, the pharmaceutical composition of the present invention has a selective inhibition activity against FGFR1, FGFR2, FGFR3 and FGFR4. Accordingly, due to the selective inhibition activity against FGFRs, the compound according to the present invention can be used to treat, prevent and alleviate myeloma, breast cancer, stomach cancer, colon cancer, bladder cancer, pancreatic cancer and hepatocellular carcinoma.

The pharmaceutical composition of the present invention contains the compound represented by Chemical Formula 1, a pharmaceutically acceptable salt thereof, a solvate thereof or a hydrate thereof as an active ingredient and may be prepared into a formulation commonly used in the pharmaceutical field, e.g., a formulation for oral administration such as a tablet, a capsule, a troche, a liquid, a suspension, etc. or a formulation for parenteral administration by adding a commonly used nontoxic, pharmaceutically acceptable carrier, adjuvant, excipient, etc.

The excipient that may be used in the pharmaceutical composition of the present invention may include a sweetener, a binder, a solubilizer, a solubilizing aid, a wetting agent, an emulsifier, an isotonic agent, an adsorbent, a disintegrant, an antioxidant, a preservative, a lubricant, a filler, an aromatic, etc. For example, lactose, dextrose, sucrose, mannitol, sorbitol, cellulose, glycine, silica, talc, stearic acid, stearin, magnesium stearate, magnesium aluminum silicate, starch, gelatin, gum tragacanth, alginic acid, sodium alginate, methylcellulose, sodium carboxymethylcellulose, agar, water, ethanol, polyethylene glycol, polyvinylpyrrolidone, sodium chloride, calcium chloride, orange essence, strawberry essence, vanilla flavor, etc. may be used.

The administration dose of the compound according to the present invention for a human may vary depending on the patient's age, body weight, sex and physical conditions, administration type or the severity of a disease. For an adult patient weighing 70 kg, the administration dose may be 0.01-1,000 mg/day in general. As per the decision by a physician or a pharmacist, the administration may be made once or several times a day with predetermined time intervals.

The present invention also provides a method for preparing the compound represented by Chemical Formula 1. The compound represented by Chemical Formula 1 according to the present invention may be prepared by a preparation method according to Scheme 1. The present invention according to the present invention is described in detail.

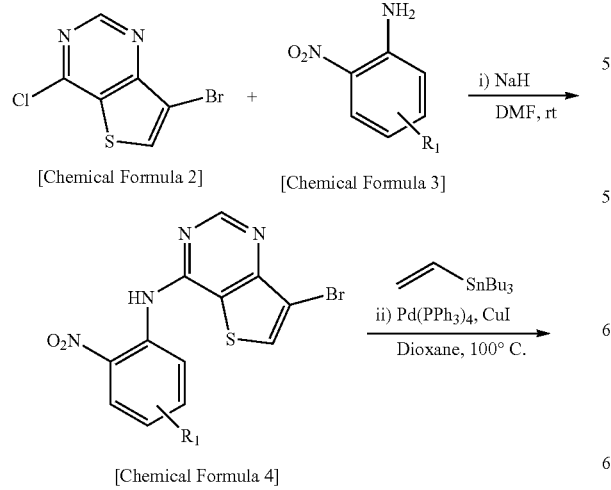

[Scheme 1]

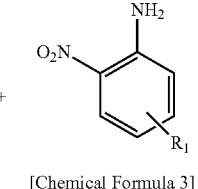

[Chemical Formula 2]    [Chemical Formula 3]

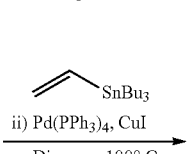

[Chemical Formula 4]

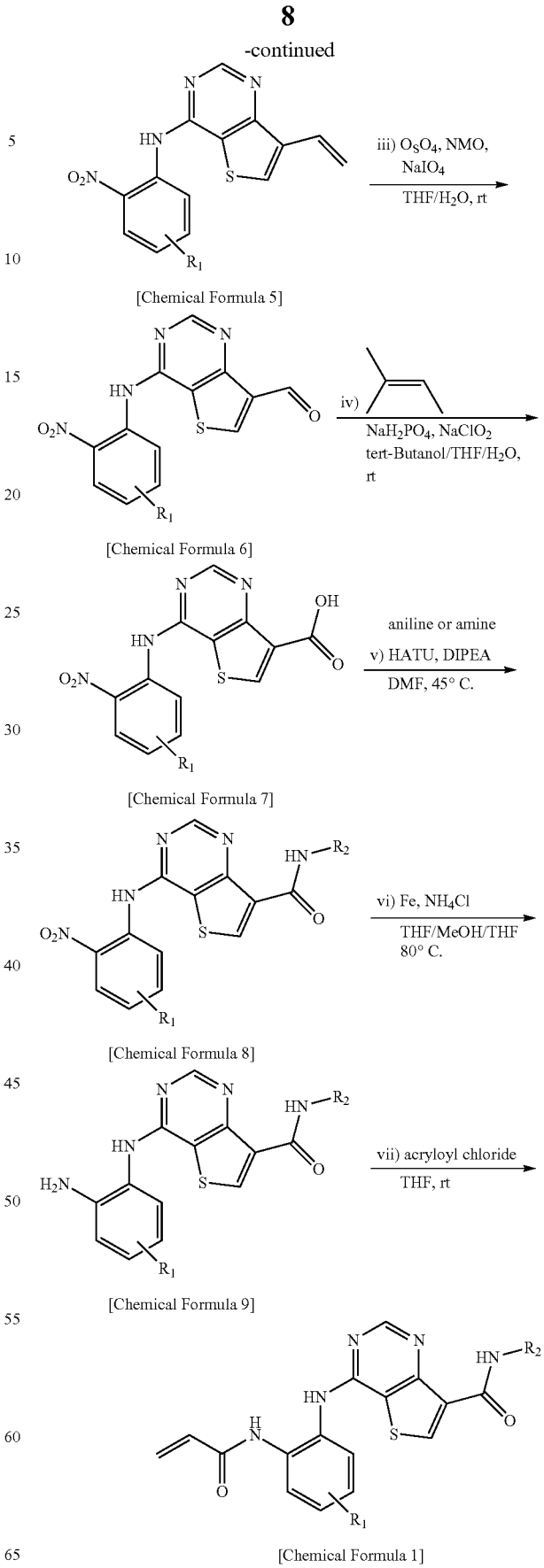

In Scheme 1, $R_1$ and $R_2$ are the same as defined above in Chemical Formula 1.

In step i), a compound represented by Chemical Formula 4 is prepared by reacting a chloro-substituted compound represented by Chemical Formula 2 with an amine compound represented by Chemical Formula 3. The reaction may be performed in the presence of a base while stirring at −20° C. to 20° C. As the base, an inorganic base selected from a hydride, hydroxide, carbonate, sulfate, etc. of an alkali metal, etc. may be used.

In step ii), a vinyl-substituted compound represented by Chemical Formula 5 is prepared by reacting the compound represented by Chemical Formula 4 with tributylvinyltin. The reaction may be conducted in the presence of a palladium catalyst and copper iodide (CuI) by heating to 70-120° C. Specifically, the palladium catalyst may be $Pd_2(dba)_3$, $Pd(OAc)_2$, $PdCl_2(PPh_3)_2$, $Pd(PPh_3)_4$, etc.

In step iii), an aldehyde compound represented by Chemical Formula 6 is prepared by oxidizing the compound represented by Chemical Formula 5. The reaction may be conducted in the presence of osmium tetroxide ($OsO_4$), N-methylmorpholine oxide (NMO) and sodium periodate ($NaIO_4$) at a temperature around room temperature, specifically at 20-30° C.

In step iv), a carboxylic acid compound represented by Chemical Formula 7 is prepared by reacting the aldehyde compound represented by Chemical Formula 6 with 2-methyl-2-butene. The reaction may be conducted in the presence of sodium biphosphate ($NaH_2PO_4$) and sodium chlorite ($NaClO_2$) at a temperature around room temperature, specifically at 20-30° C.

In step v), an amide compound represented by Chemical Formula 8 is prepared by reacting the carboxylic acid compound represented by Chemical Formula 7 with an amine compound represented by $R_2$—$NH_2$. In order to facilitate the coupling reaction, a catalyst such as 1,3-dicyclohexylcarbodiimide (DCC), 1-ethyl-3-(3-dimethylaminopropyl)carbodiimide (EDC), 1-[bis(dimethylamino)methylene-1H-1,2,3-triazolo[4,5-b]pyridinium 3-oxide hexafluorophosphate (HATU), etc. may be used. As an additive, an organic base such as triethylamine (TEA), N,N-diisopropylethylamine (DIPEA), etc. or an alkali metal carbonate as an inorganic base such as $Cs_2CO_3$, $K_2CO_3$ and $NaHCO_3$ may be used. The coupling reaction may be conducted by heating to 30-80° C.

In step vi), an amine compound represented by Chemical Formula 9 is prepared reducing the amide compound represented by Chemical Formula 8, thereby converting the nitro group to an amine group. The reduction reaction may be conducted in the presence of Fe and ammonium chloride ($NH_4Cl$) by heating to 40-100° C.

In step vii), the target compound represented by Chemical Formula 1 is prepared by reacting the amine compound represented by Chemical Formula 9 with acryloyl chloride. The reaction may be conducted at a temperature around room temperature, specifically at 20-30° C.

As a reaction solvent used in the respective preparation steps according to Scheme 1, water or a commonly used organic solvent including tetrahydrofuran (THF), dichloromethane, dioxane, N,N-dimethylformamide (DMF), N,N-dimethyl sulfoxide (DMSO), 2-butanol, 2-pentanol, etc. may be used. If necessary, they may be used in appropriate combinations.

The intermediate compounds synthesized during the preparation method according to Scheme 1 are novel compounds and they are very useful as intermediates in the synthesis process of the compound represented by Chemical Formula 1.

Accordingly, the present invention provides a novel intermediate compound represented by Chemical Formula 4, Chemical Formula 5, Chemical Formula 6 or Chemical Formula 7, which is prepared during the preparation process according to Scheme 1.

The present invention will be described in more detail through examples, formulation examples and test examples. The following examples, formulation examples and test examples are for illustrative purposes only and it will be apparent to those skilled in the art that the scope of this invention is not limited by them.

EXAMPLES

Example 1. Preparation of 4-((2-acrylamido-6-methylphenyl)amino)-N-(3,5-dimethoxyphenyl)thieno[3,2-d]pyrimidine-7-carboxamide (Compound 1)

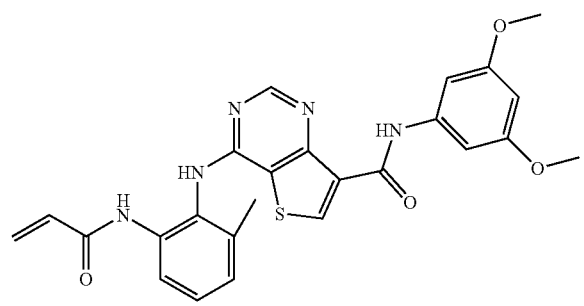 [SMILES: C=CC(=O)Nc1cccc(C)c1Nc1ncnc2c(C(=O)Nc3cc(OC)cc(OC)c3)csc12]

Step 1: 7-Bromo-N-(2-methyl-6-nitrophenyl)thieno[3,2-d]pyrimidin-4-amine

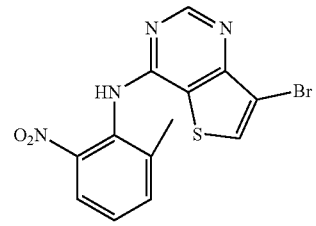 [SMILES: Cc1cccc([N+](=O)[O-])c1Nc1ncnc2c(Br)csc12]

2-Methyl-6-nitroaniline (42.1 mmol, 6.5 g) and dimethylformamide (130 mL) were added to a round-bottom flask. After adding sodium hydride (5.7 g, 38.3 mmol) at 0° C., the mixture was stirred for 30 minutes. Then, 7-bromo-4-chlorothieno[3,2-d]pyrimidine (10.0 g, 38.3 mmol) was added and the mixture was stirred at room temperature for 1 hour. Upon completion of reaction, the reaction mixture was diluted with ethyl acetate and then neutralized (pH=7) by slowly adding a 1 N HCl aqueous solution dropwise at 0° C. After separating an aqueous layer from an organic layer, the aqueous layer was extracted with ethyl acetate. The combined organic layer was dried with sodium sulfate and then concentrated under reduced pressure. The resulting mixture was purified by MPLC to obtain the desired target compound.

$^1$H NMR (400 MHz, CDCl$_3$) δ 8.78 (s, 1H), 7.97-7.95 (m, 1H), 7.82-7.81 (m, 1H), 7.63-7.61 (m, 1H), 7.45-7.42 (m, 1H), 2.32 (s, 3H).

Step 2: N-(2-Methyl-6-nitrophenyl)-7-vinylthieno[3,2-d]pyrimidin-4-amine

7-Bromo-N-(2-methyl-6-nitrophenyl)thieno[3,2-d]pyrimidin-4-amine (2.5 g, 6.85 mmol) and tributylvinyltin (2.4 mL, 7.54 mmol) were added to a round-bottom flask and then dissolved by adding 1,4-dioxane (68.5 mL). After adding Pd(PPh$_3$)$_4$ (785 mg, 0.68 mmol), the mixture was stirred at 100° C. for 15 hours. The reaction mixture was cooled to room temperature and then extracted with ethyl acetate and a sodium bicarbonate aqueous solution. The combined organic layer was washed with brine, dried with sodium sulfate and then concentrated under reduced pressure. The resulting mixture was purified by MPLC to obtain the desired target compound (1.4 g, 66%).

$^1$H NMR (400 MHz, CDCl$_3$) δ 8.71 (s, 1H), 8.24 (bs, 1H), 7.94-7.92 (m, 1H), 7.71 (s, 1H), 7.60-7.58 (m, 1H), 7.40-7.36 (m, 1H), 7.07-7.00 (m, 1H), 6.29-6.24 (m, 1H), 5.49-5.46 (m, 1H), 2.30 (s, 3H).

Step 3: 4-((2-Methyl-6-nitrophenyl)amino)thieno[3,2-d]pyrimidine-7-carbaldehyde

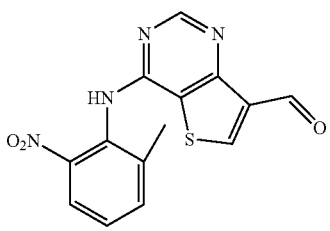 [SMILES: Cc1cccc([N+](=O)[O-])c1Nc1ncnc2c(C=O)csc12]

N-(2-Methyl-6-nitrophenyl)-7-vinylthieno[3,2-d]pyrimidin-4-amine (1.4 g, 4.49 mmol) was added to a round-bottom flask and then dissolved by adding tetrahydrofuran/water (2.5:1, 31.45 mL). Then, N-methylmorpholine oxide (4.3 mL, 17.96 mmol, 50 w/w % aqueous solution) and osmium tetroxide (2.85 mL, 0.45 mmol, 4 w/w % aqueous solution) were added at 0° C. After stirring at room temperature for 7 hours, reaction was terminated by using a sodium sulfite solution and the aqueous layer was extracted several times using ethyl acetate. The combined organic layer was dried by distilling under reduced pressure and the obtained residue was dissolved by adding tetrahydrofuran/water (2.5:1, 31.45 mL). Then, after adding NaIO$_4$ (1.90 g, 8.98 mmol), the mixture was stirred at room temperature for 1 hour. Upon completion of reaction, suspended materials were filtered using celite and washed several times with ethyl acetate. The obtained residue was extracted using water and ethyl acetate, dried with sodium sulfate and then concentrated under reduced pressure. The resulting mixture was purified by MPLC to obtain the desired target compound (1.0 g, 71%).

$^1$H NMR (400 MHz, DMSO-d$_6$) δ 10.29 (s, 1H), 9.97 (bs, 1H), 9.04 (s, 1H), 8.52 (s, 1H), 7.90-7.88 (m, 1H), 7.74-7.72 (m, 1H), 7.55-7.51 (m, 1H), 2.29 (s, 3H).

Step 4: 4-((2-Methyl-6-nitrophenyl)amino)thieno[3,2-d]pyrimidine-7-carboxylic acid

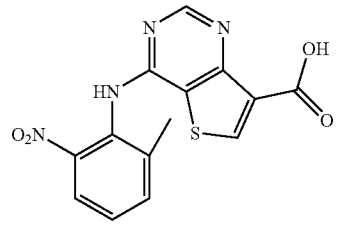 [SMILES: Cc1cccc([N+](=O)[O-])c1Nc1ncnc2c(C(=O)O)csc12]

4-((2-Methyl-6-nitrophenyl)amino)thieno[3,2-d]pyrimidine-7-carbaldehyde (1.0 g, 3.18 mmol) was added to a round-bottom flask and dissolved in tetrahydrofuran/tert-butanol/water (1:1:1, 28.6 mL). After adding 2-methyl-2-butene (2.39 mL, 4.77 mmol, 2 M in tetrahydrofuran) at 0° C., NaH$_2$PO$_4$ (2.10 g, 49.39 mmol) and NaClO$_2$ (0.95 g, 10.49 mmol) were added 5 minutes later. The mixture was stirred at room temperature for 6 hours. Upon completion of reaction, the aqueous layer was extracted several times using a chloroform/isopropyl alcohol (4:1) solvent. The obtained organic layer was dried with sodium sulfate and then concentrated under reduced pressure to obtain the target compound (805 mg, 77%).

$^1$H NMR (400 MHz, DMSO-d$_6$) δ 10.08 (bs, 1H), 8.97 (s, 1H), 8.51 (s, 1H), 7.90-7.88 (m, 1H), 7.75-7.73 (m, 1H), 7.53 (s, 1H), 2.28 (s, 3H).

Step 5: N-(3,5-Dimethoxyphenyl)-4-((2-methyl-6-nitrophenyl)amino)thieno[3,2-d]pyrimidine-7-carboxamide

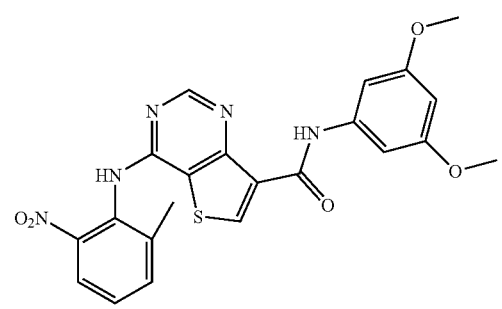

4-((2-Methyl-6-nitrophenyl)amino)thieno[3,2-d]pyrimidine-7-carboxylic acid (100 mg, 0.30 mmol), HATU (345 mg, 0.91 mmol) and DIPEA (0.28 mL, 1.52 mmol) were added to a round-bottom flask and dissolved in dimethylformamide (5 mL). Then, 3,5-dimethoxyaniline (47 mg, 0.30 mmol) was added and the mixture was stirred at 45° C. for 15 hours. Upon completion of reaction, the reaction mixture was extracted with ethyl acetate and a sodium bicarbonate aqueous solution. The combined organic layer was washed with brine, dried with sodium sulfate and then concentrated under reduced pressure.

$^1$H NMR (400 MHz, DMSO-d$_6$) δ 10.08 (bs, 1H), 8.95 (s, 1H), 8.62 (s, 1H), 7.89 (d, J=8.8 Hz, 1H), 7.74 (d, J=7.2 Hz, 1H), 7.53 (m, 1H), 6.99 (d, J=2.0 Hz, 1H), 6.32 (m, 1H), 3.78 (s, 6H), 2.30 (s, 3H). MS m/z: 466 [M+1].

Step 6: 4-((2-Amino-6-methylphenyl)amino)-N-(3,5-dimethoxyphenyl)thieno[3,2-d]pyrimidine-7-carboxamide

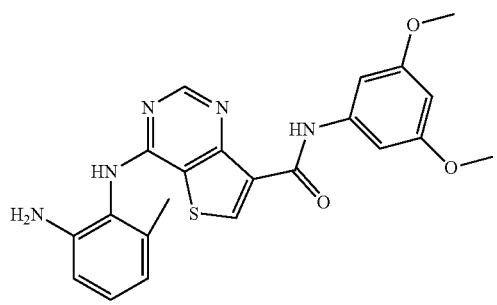 [SMILES: COc1cc(NC(=O)c2csc3c(Nc4c(C)cccc4[N+](=O)[O-])ncnc23)cc(OC)c1]

The mixture obtained in step 5 was dissolved in tetrahydrofuran/methanol/water (4:2:1, 1.05 mL). Then, after adding Fe (30.3 mg, 0.61 mmol) and NH$_4$Cl (64.2 mg, 1.21 mmol), the mixture was stirred at 80° C. for 3 hours. Upon completion of reaction, the reaction mixture was filtered with celite and washed several times with ethyl acetate. The filtrate was extracted using water and ethyl acetate. The combined organic layer was washed with brine, dried with sodium sulfate and then concentrated under reduced pressure.

MS m/z: 436 [M+1].

Step 7: 4-((2-Acrylamido-6-methylphenyl)amino)-N-(3,5-dimethoxyphenyl)thieno[3,2-d]pyrimidine-7-carboxamide The mixture obtained in step 6 was dissolved in tetrahydrofuran (6 mL). Then, after adding acryloyl chloride (0.25 mL, 3.03 mmol) at 0° C., the mixture was stirred at room temperature for 30 minutes. Upon completion of reaction, water (1 mL) was slowly added dropwise and the mixture was stirred at room temperature for 10 minutes. The reaction mixture was extracted using water and ethyl acetate. The combined organic layer was washed with brine, dried with sodium sulfate and then concentrated under reduced pressure. The target compound was obtained by MPLC.

MS m/z: 490 [M+1].

Examples 2-9

Compounds 2-9 were obtained as target compounds in the same manner as in Example 1, except for using different amine or aniline in step 5 instead of 3,5-dimethoxyaniline.

TABLE 1

| Compound number | Chemical structure | MS(m/z) |
|---|---|---|
| 2 | 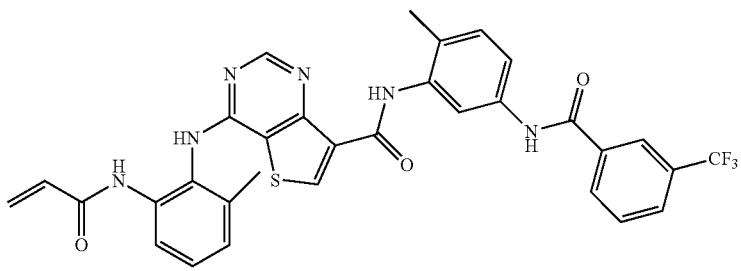 [SMILES: C=CC(=O)Nc1cccc(C)c1Nc1ncnc2c(C(=O)Nc3cc(NC(=O)c4cccc(C(F)(F)F)c4)ccc3C)csc12] | 631 |
| 3 | 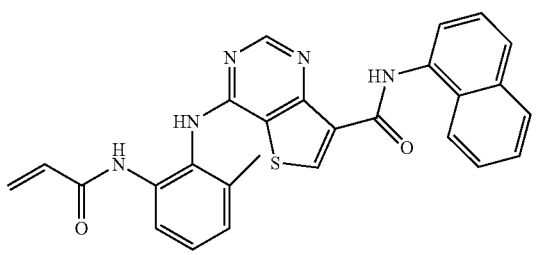 [SMILES: C=CC(=O)Nc1cccc(C)c1Nc1ncnc2c(C(=O)Nc3cccc4ccccc34)csc12] | 480 |

TABLE 1-continued

| Compound number | Chemical structure | MS(m/z) |
|---|---|---|
| 4 | 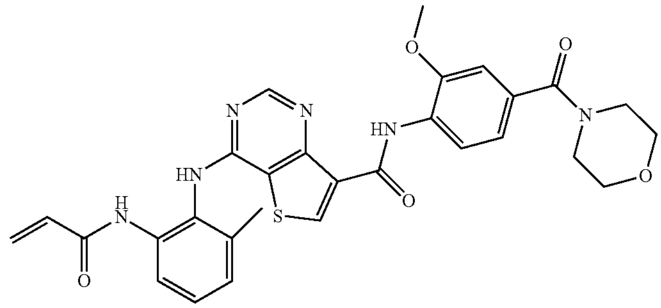 [SMILES: C=CC(=O)Nc1cccc(C)c1Nc1ncnc2c(C(=O)Nc3ccc(C(=O)N4CCOCC4)cc3OC)csc12] | 573 |
| 5 | 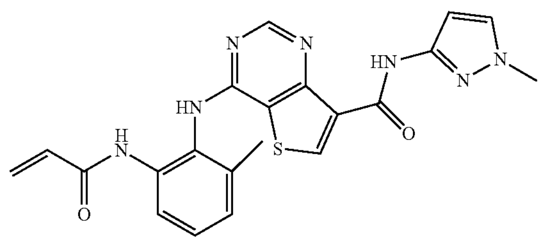 [SMILES: C=CC(=O)Nc1cccc(C)c1Nc1ncnc2c(C(=O)Nc3ccn(C)n3)csc12] | 434 |
| 6 | 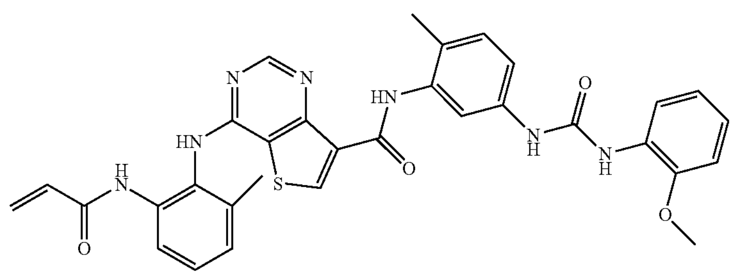 [SMILES: C=CC(=O)Nc1cccc(C)c1Nc1ncnc2c(C(=O)Nc3cc(NC(=O)Nc4ccccc4OC)ccc3C)csc12] | 608 |
| 7 | 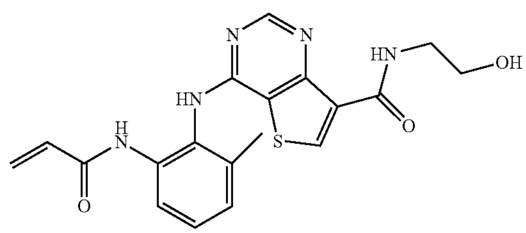 [SMILES: C=CC(=O)Nc1cccc(C)c1Nc1ncnc2c(C(=O)NCCO)csc12] | 398 |
| 8 | 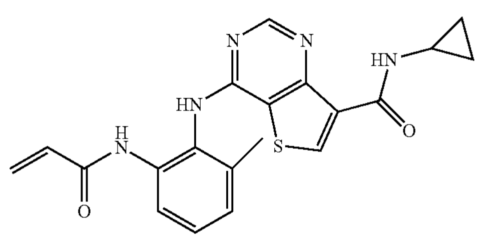 [SMILES: C=CC(=O)Nc1cccc(C)c1Nc1ncnc2c(C(=O)NC3CC3)csc12] | 394 |
| 9 | 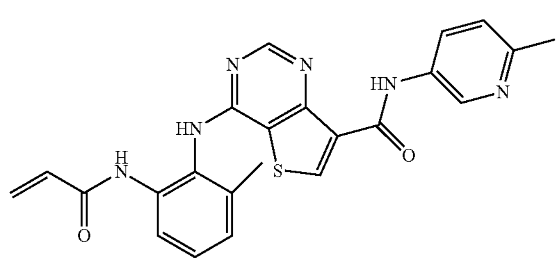 [SMILES: C=CC(=O)Nc1cccc(C)c1Nc1ncnc2c(C(=O)Nc3ccc(C)nc3)csc12] | 445 |

TEST EXAMPLES

Test Example 1. Measurement of Protein Kinase Inhibition Activity

The protein kinase inhibition activity of 4-((2-acrylamido-6-methylphenyl)amino)-N-(2-methyl-5-(3-(trifluoromethyl)benzamido)phenyl)thieno[3,2-d]pyrimidine-7-carboxamide (Compound 2) synthesized in the present invention was measured.

Test Example 2. Measurement of Ability of Inhibiting Growth of Liver Cancer Cell Lines Hep3B and HUH7

The inhibition activity for liver cancer cell lines was measured for 4-((2-acrylamido-6-methylphenyl)amino)-N-(3,5-dimethoxyphenyl)thieno[3,2-d]pyrimidine-7-carboxamide (Compound 1) and 4-((2-acrylamido-6-methylphenyl)amino)-N-(2-methyl-5-(3-(trifluoromethyl)benzamido)phenyl)thieno[3,2-d]pyrimidine-7-carboxamide (Compound 2) synthesized in the present invention.

Hep3B or HUH7 cells were seeded onto a 96-well plate with 5,000 cells per well and then cultured overnight in F-12K Nutrient Mixture (Life Technologies Corporation) containing 10% FBS at 37° C. in the presence of 5% $CO_2$. The test compound dissolved in dimethyl sulfoxide was diluted to a final concentration of 1-50 μM and then added to the 96-well plate. After culturing at 37° C. in the presence of 5% $CO_2$ and adding a cell count reagent (CellTiter-Glo® Luminescent Cell Viability Assay), luminescence intensity was measured using a luminescence measuring apparatus (Envision). The result is shown in Table 2.

TABLE 2

| Test compounds | $GI_{50}$ (μM) | |
| --- | --- | --- |
| | Hep3B | HUH7 |
| Compound 1 | <10 | <10 |
| Compound 2 | <1 | <1 |

The novel compound represented by Chemical Formula 1 according to the present invention can be prepared into various types of formulations depending on purposes. The followings are some formulation examples containing the compound represented by Chemical Formula 1 according to the present invention as an active ingredient. However, the present invention is not limited by them.

[FORMULATION EXAMPLES] PREPARATION OF PHARMACEUTICAL FORMULATIONS

Formulation Example 1. Tablet (Direct Compression)

After sieving 5.0 mg of the active ingredient and mixing with 14.1 mg of lactose, 0.8 mg of crospovidone USNF and 0.1 mg of magnesium stearate, the mixture was compressed into a tablet.

Formulation Example 2. Tablet (Wet Granulation)

5.0 mg of the active ingredient was sieved and mixed with 16.0 mg of lactose and 4.0 mg of starch. After dissolving 0.3 mg of polysorbate 80 in pure water, an adequate amount of the solution was added and the mixture was prepared into fine granules. After drying and sieving, the fine granules were mixed with 2.7 mg of colloidal silicon dioxide and 2.0 mg of magnesium stearate. The fine granules were compressed into a tablet.

Formulation Example 3. Powder and Capsule 5.0 mg of the active ingredient was sieved and mixed with 14.8 mg of lactose, 10.0 mg of polyvinylpyrrolidone and 0.2 mg of magnesium stearate. The mixture was filled in a hard No. 5 gelatin capsule using an adequate apparatus.

Formulation Example 4. Injection

An injection was prepared using 100 mg of the active ingredient, 180 mg of mannitol, 26 mg of $Na_2HPO_4.12H_2O$ and 2974 mg of distilled water.

The present invention has been described in detail with reference to specific embodiments thereof. However, it will be appreciated by those skilled in the art that various changes and modifications may be made in these embodiments without departing from the principles and spirit of the invention, the scope of which is defined in the appended claims and their equivalents.

What is claimed is:

1. A compound of formula (1), a pharmaceutically acceptable salt thereof, or a stereoisomer thereof:

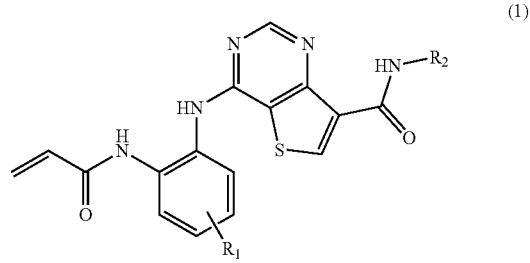

(1)

wherein:
$R_1$ is a hydrogen atom or a $C_1$-$C_6$ alkyl group,
$R_2$ is a $C_1$-$C_6$ alkyl group, a $C_1$-$C_6$ hydroxyalkyl group, a $C_6$-$C_{12}$ aryl group or a 5- or 6-membered heteroaryl group containing 1-3 nitrogen atom(s), and
the aryl group or the heteroaryl group may be respectively substituted or unsubstituted with 1-2 substituent(s) selected from the group consisting of $C_1$-$C_6$ alkyl, a halogen, $C_1$-$C_6$ alkoxy,

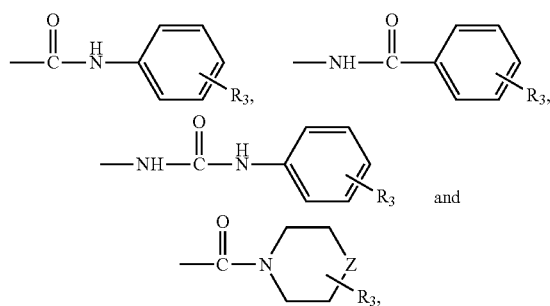

wherein Z is $CHR_3$, $NR_3$ or O and $R_3$ is a hydrogen atom, a $C_1$-$C_6$ alkyl group, a $C_1$-$C_6$ haloalkyl group or a $C_1$-$C_6$ alkoxy group.

2. The compound according to claim 1, wherein $R_1$ is a $C_1$-$C_6$ alkyl group and $R_2$ is a $C_1$-$C_6$ alkyl group or a $C_1$-$C_6$ hydroxyalkyl group.

3. The compound according to claim 1, wherein
$R_1$ is a $C_1$-$C_6$ alkyl group,
$R_2$ is a phenyl group or a naphthalenyl group, and
the phenyl group may be substituted or unsubstituted with 1-2 substituent(s) selected from the group consisting of $C_1$-$C_6$ alkyl, $C_1$-$C_6$ alkoxy,

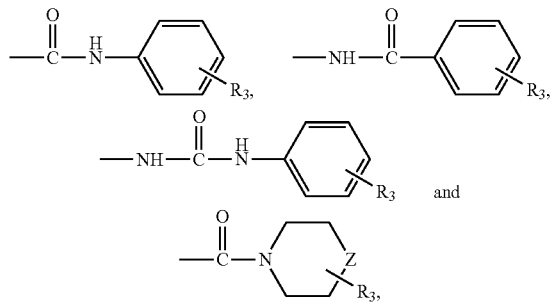

wherein Z is an oxygen (O) atom and $R_3$ is a $C_1$-$C_6$ alkyl group, a $C_1$-$C_6$ haloalkyl group or a $C_1$-$C_6$ alkoxy group.

4. The compound according to claim 1, wherein
$R_1$ is a $C_1$-$C_6$ alkyl group,
$R_2$ is a pyrazolyl group or a pyridinyl group, and
the pyrazolyl group or the pyridinyl group may be respectively substituted or unsubstituted with 1-2 substituent(s) selected from $C_1$-$C_6$ alkyl group.

5. The compound according to claim 1, which is selected from the group consisting of:
- 4-((2-acrylamido-6-methylphenyl)amino)-N-(3,5-dimethoxyphenyl)thieno[3,2-d]pyrimidine-7-carboxamide;
- 4-((2-acrylamido-6-methylphenyl)amino)-N-(2-methyl-5-(3-(trifluoromethyl)benzamido)phenyl)thieno[3,2-d]pyrimidine-7-carboxamide;
- 4-((2-acrylamido-6-methylphenyl)amino)-N-(naphthalen-1-yl)thieno[3,2-d]pyrimidine-7-carboxamide;
- 4-((2-acrylamido-6-methylphenyl)amino)-N-(2-methoxy-4-(morpholine-4-carbonyl)phenyl)thieno[3,2-d]pyrimidine-7-carboxamide;
- 4-((2-acrylamido-6-methylphenyl)amino)-N-(1-methyl-1H-pyrazol-3-yl)thieno[3,2-d]pyrimidine-7-carboxamide;
- 4-((2-acrylamido-6-methylphenyl)amino)-N-(5-(3-(2-methoxyphenyl)ureido)-2-methylphenyl)thieno[3,2-d]pyrimidine-7-carboxamide;
- 4-((2-acrylamido-6-methylphenyl)amino)-N-(2-hydroxyethyl)thieno[3,2-d]pyrimidine-7-carboxamide;
- 4-((2-acrylamido-6-methylphenyl)amino)-N-cyclopropylthieno[3,2-d]pyrimidine-7-carboxamide;
- 4-((2-acrylamido-6-methylphenyl)amino)-N-(6-methylpyridin-3-yl)thieno[3,2-d]pyrimidine-7-carboxamide;

or a pharmaceutically acceptable salt thereof or a stereoisomer thereof.

6. A pharmaceutical composition comprising:
the compound or a pharmaceutically acceptable salt thereof according to claim 1, and
a pharmaceutically acceptable carrier, adjuvant, or excipient.

7. A compound represented by Chemical Formula 4, Chemical Formula 5, Chemical Formula 6 or Chemical Formula 7:

[Chemical Formula 4]

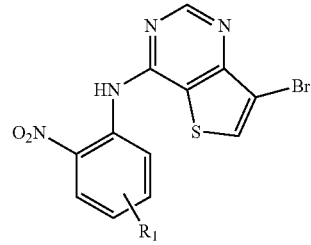

[Chemical Formula 5]

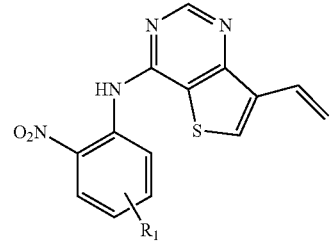

[Chemical Formula 6]

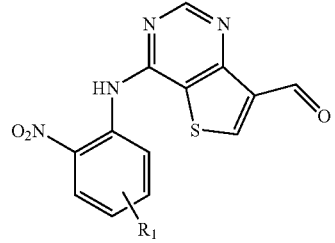

[Chemical Formula 7]

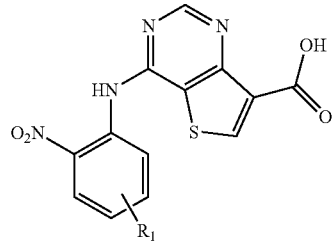

wherein $R_1$ is a hydrogen atom or a $C_1$-$C_6$ alkyl group.

8. A pharmaceutical composition comprising:
the compound or pharmaceutically acceptable salt thereof according to claim 5, and
a pharmaceutically acceptable carrier, adjuvant, or excipient.

* * * * *